(12) United States Patent
Mori et al.

(10) Patent No.: US 11,442,951 B2
(45) Date of Patent: Sep. 13, 2022

(54) INFORMATION PROCESSING APPARATUS, CLIENT TERMINAL, AND PROGRAM

(71) Applicant: SHISEIDO COMPANY, LTD., Tokyo (JP)

(72) Inventors: Yuichiro Mori, Kanagawa (JP); Naoki Saito, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 266 days.

(21) Appl. No.: 16/612,446

(22) PCT Filed: Aug. 17, 2018

(86) PCT No.: PCT/JP2018/030481
§ 371 (c)(1),
(2) Date: Nov. 11, 2019

(87) PCT Pub. No.: WO2019/039393
PCT Pub. Date: Feb. 28, 2019

(65) Prior Publication Data
US 2020/0097465 A1    Mar. 26, 2020

(30) Foreign Application Priority Data

Aug. 22, 2017 (JP) .............................. JP2017-159667

(51) Int. Cl.
*G06F 16/248* (2019.01)
*G01J 1/42* (2006.01)

(52) U.S. Cl.
CPC ............ *G06F 16/248* (2019.01); *G01J 1/429* (2013.01)

(58) Field of Classification Search
CPC .............................. G06F 16/248; G01J 1/429
(Continued)

(56) References Cited

U.S. PATENT DOCUMENTS

2010/0169220 A1    7/2010 Choing et al.
2010/0241464 A1    9/2010 Amigo et al.
(Continued)

FOREIGN PATENT DOCUMENTS

JP    2001-212087 A    8/2001
JP    2002-015068 A    1/2002
(Continued)

OTHER PUBLICATIONS

International Search Report (with partial translation) dated Nov. 13, 2018, issued in corresponding International Patent Application No. PCT/JP2018/030481.
(Continued)

*Primary Examiner* — Joshua Bullock
(74) *Attorney, Agent, or Firm* — Morgan, Lewis & Bockius LLP

(57) ABSTRACT

Optimal information in consideration with time series environmental factors is provided to users.
The information processing apparatus includes a retrieve module configured to retrieve environmental information indicating an ultraviolet ray exposure amount indicating an amount of ultraviolet rays exposed to a user, a temperature of an environment where the user stays, and a humidity of the environment where the user stays, a present module configured to present first information relating to the skin condition of the user based on the environmental information, and a present module configured to present second information relating to the skin condition of the user based on environmental log information including a plurality of environmental information.

10 Claims, 15 Drawing Sheets

(58) Field of Classification Search
USPC .......................................................... 707/722
See application file for complete search history.

(56) References Cited

U.S. PATENT DOCUMENTS

| | | | |
|---|---|---|---|
| 2015/0045631 A1* | 2/2015 | Ademola | A61B 5/6898 |
| | | | 600/301 |
| 2016/0331308 A1* | 11/2016 | Zhou | A61B 5/0022 |
| 2017/0189751 A1 | 7/2017 | Knickerbocker et al. | |
| 2019/0142138 A1* | 5/2019 | Chen | A45D 44/005 |
| | | | 132/200 |

FOREIGN PATENT DOCUMENTS

| | | |
|---|---|---|
| JP | 2002-041959 A | 2/2002 |
| JP | 2006-285451 A | 10/2006 |
| WO | 2016/063190 A1 | 4/2016 |

OTHER PUBLICATIONS

Extended EP Search Report dated Dec. 15, 2020, issued in corresponding International Patent Application No. PCT/JP2018/030481.

\* cited by examiner

| USER INFORMATION DATABASE | | | | |
|---|---|---|---|---|
| USER ID | USER NAME | USER ATTRIBUTE | | ESTIMATION FORMULA |
| | | GENDER | AGE | |
| U001 | U1 | FEMALE | 28 | f=a1*T+b1*M+c1*UV··· |
| U002 | U2 | MALE | 30 | f=a2*T+b2*M+c2*UV··· |
| ▪ | ▪ | ▪ | ▪ | ▪ |

FIG. 3

| ENVIORMENTAL INFORMATION DATABASE (USER ID = U001) | | | | |
| --- | --- | --- | --- | --- |
| ENVIORMENTAL LOG ID | DATE AND TIME | UV EXPOSURE | TEMP | HUM |
| ELOG001 | 2017/5/1 10:00 | ▪ | ▪ | ▪ |
| ELOG002 | 2017/5/1 11:00 | ▪ | ▪ | ▪ |
| ▪ | ▪ | ▪ | ▪ | ▪ |

FIG. 4

| ACTION LOG INFORMATION DATABASE (USER ID = U001) | | | | | | |
|---|---|---|---|---|---|---|
| ACTION LOG ID | DATE AND TIME | ACTION | START TIME | END TIME | CALORIE CHANGE | POSITION |
| ALOG001 | 2017/5/1 8:00 | MEAL | 7:30 | 8:00 | +200 | X1, Y1 |
| ALOG002 | 2017/5/1 9:00 | RUNNNING | 8:30 | 9:00 | -500 | X2, Y2 |
| ALOG003 | 2017/5/1 12:00 | MEAL | 11:30 | 12:00 | +400 | X3, Y3 |
| ALOG004 | 2017/5/1 19:00 | MEAL | 18:00 | 19:00 | +1500 | X4, Y4 |
| ALOG005 | 2017/5/2 8:00 | SLEEPING | 22:00 | 8:00 | -1 | X1, Y1 |
| ALOG006 | 2017/5/2 8:00 | SKIN CARE | 22:00 | 22:30 | -5 | X1, Y1 |
| . | . | . | . | . | . | . |

FIG. 5

| MIND-BODY LOG INFORMATION DATABASE (USER ID = U001) |||||
|---|---|---|---|---|
| MIND-BODY LOG ID | DATE AND TIME | PULSE | SEXUAL CYCLE | STRESS |
| BLOG001 | 2017/5/1 8:00 | 90 | ▪ | ▪ |
| BLOG002 | 2017/5/1 9:00 | 60 | ▪ | ▪ |
| ▪ | ▪ | ▪ | ▪ | ▪ |

FIG. 6

| SKIN EVALUATION LOG INFORMATION DATABASE (USER ID = U001) ||||
|---|---|---|---|
| SKIN EVALUATION LOG ID | DATE AND TIME | SKIN SCORE ||
| ||FIRST SKIN SCORE | SECOND SKIN SCORE |
| EST001 | 2017/5/1 8:00 | 80 | 70 |
| EST002 | 2017/5/1 22:00 | 70 | 90 |
| EST003 | 2017/5/2 22:00 | 90 | 80 |
| EST004 | 2017/5/2 | 30 | 50 |
| ▪ | ▪ | ▪ | ▪ |

FIG. 7

| CONTENT MATCHING TABLE | | |
| --- | --- | --- |
| REFERENCE SCORE | REAL-TIME CONTENT | ONE-TIME CONTENT |
| 20-39 | REAL001 | ONE001 |
| 40-59 | REAL002 | ONE002 |
| 60-89 | REAL003 | ONE003 |
| ▪ | ▪ | ▪ |

FIG. 8

| TASK INFORMATION DATABASE (USER ID = U001) | | | |
|---|---|---|---|
| TASK ID | REFERENCE CONTENTS | REGISTRATION DATE AND TIME | END DATE AND TIME |
| TSK001 | REAL001 | 2017/5/1 10:00 | NOT |
| TSK002 | ONE003 | 2017/5/1 23:25 | 2017/5/1 23:50 |
| ▪ | ▪ | ▪ | ▪ |

FIG. 9

INFORMATION PROCESSING APPARATUS, CLIENT TERMINAL, AND PROGRAM

TECHNICAL FIELD

A present invention relates to an information processing apparatus, a client apparatus, and a program.

BACKGROUND ART

Generally, it is known that human skin is affected by environmental factors (for example, ultraviolet rays, temperature, and humidity).

For example, cosmetic stores provide advice in accordance with the environmental factors of the environment where a customer stay.

The customer selects cosmetics to purchase in consideration of the provided advice.

Conventionally, a technique for providing advice on skin care in consideration of environmental factors of the environment where the user stays.

For example, Patent Document 1 discloses a system that presents advice on a skin care method according to the amount of ultraviolet rays exposed to a user.

PRIOR ART DOCUMENTS

Patent Documents

[Patent Document 1] Japanese Patent Laid-Open No. 2002-41959

SUMMARY OF INVENTION

Technical Problem

Human skin is not only a temporary environmental factor, also affected by time-series environmental factors.

That is, advice that considers only the environmental factors at a point in time is not optimal advice for the user.

However, the system of Patent Document 1 provides advice information based on ultraviolet exposure information retrieved from a measuring apparatus.

The ultraviolet radiation exposure information retrieved from the measuring apparatus is a temporary environmental factor.

That is, this system does not consider time-series environmental factors.

Therefore, the advice information of Patent Document 1 is not optimum advice for the user.

An object of the present invention is to provide a user with optimal information in consideration of time-series environmental factors.

Solution to Problem

One aspect of the present invention is an information processing apparatus comprising;

a retrieve module configured to retrieve environmental information indicating an ultraviolet ray exposure amount indicating an amount of ultraviolet rays exposed to a user, a temperature of an environment where the user stays, and a humidity of the environment where the user stays;

a present module configured to present first information relating to the skin condition of the user based on the environmental information; and present module configured to present second information relating to the skin condition of the user based on environmental log information including a plurality of environmental information.

Advantageous Effects of Invention

According to the present invention, it is possible to provide the user with optimal information in consideration of time-series environmental factors.

BRIEF DESCRIPTION OF DRAWINGS

FIG. 3 is a diagram showing a data structure of a user information database according to the present embodiment.

FIG. 4 is a view showing a data structure of an environment log information database according to the embodiment.

FIG. 5 is a diagram showing a data structure of an action log information database according to the present embodiment.

FIG. 6 is a diagram showing a data structure of a mind-body log information database according to the present embodiment.

FIG. 7 is a diagram showing a data structure of a skin evaluation log information database according to the present embodiment.

FIG. 8 is a diagram showing a data structure of a content matching table according to the present embodiment.

FIG. 9 is a view showing a data structure of a task information database according to the embodiment.

DESCRIPTION OF EMBODIMENTS

Figure 1:
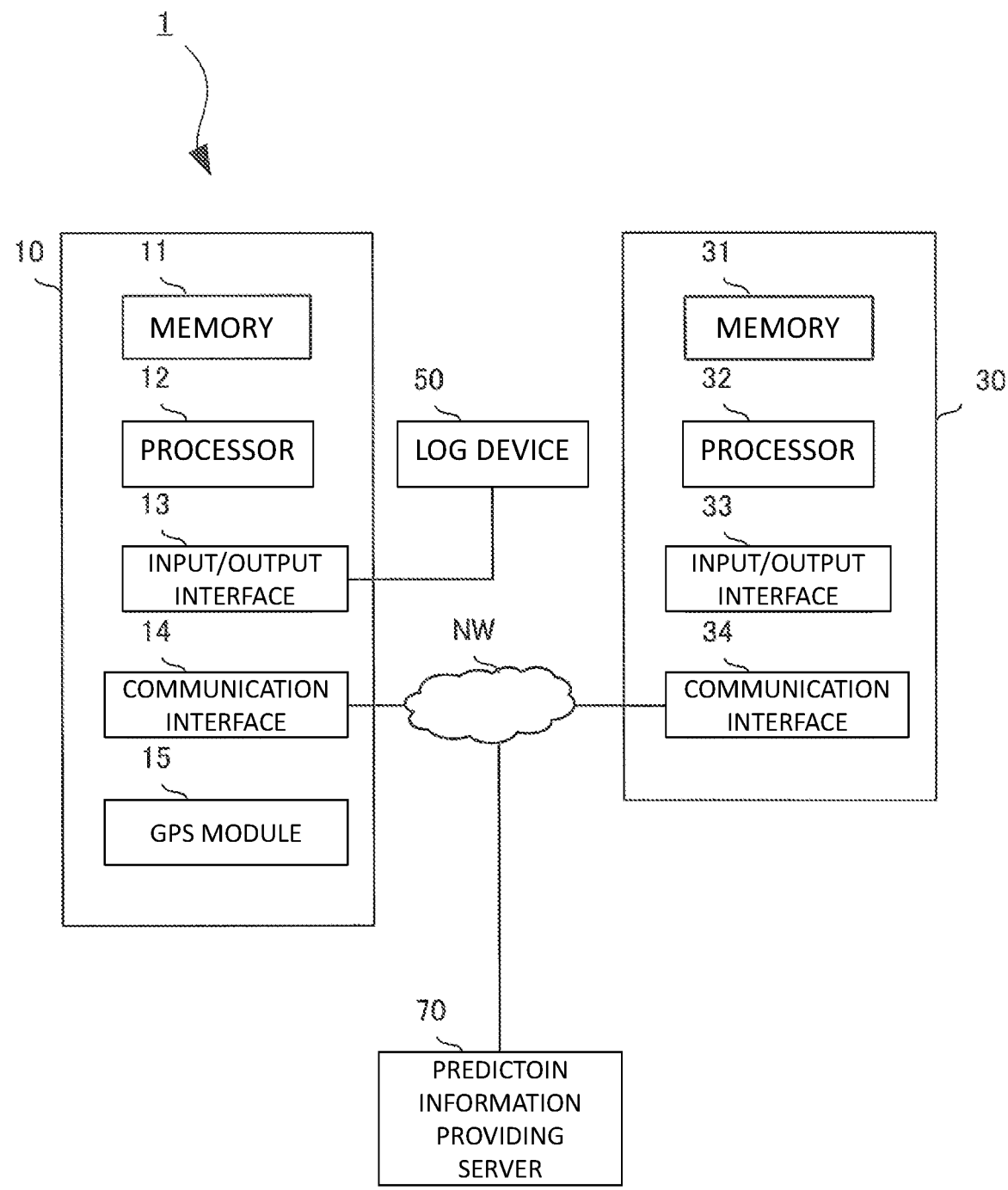
FIG. 1 is a block diagram showing a configuration of an information processing system according to the present embodiment.

Hereinafter, an embodiment of the present invention will be described in detail with reference to the drawings.

Note that, in the drawings for describing the embodiments, the same components are denoted by the same reference sign in principle, and the repetitive description thereof is omitted.

(1) Configuration of Information Configuration of Information Processing System

A information processing system of the present embodiment will be described.

FIG. 1 is a block diagram showing the configuration of the information processing system according to the present embodiment.

As shown in FIG. 1, the information processing system 1 includes a client apparatus 10, a server 30, a log device 50

(an example of a measurement apparatus), and a prediction information providing server 70.

The client apparatus 10, the server 30, and the prediction information providing server 70 are connected via a network (for example, an Internet or an intranet) NW.

The client apparatus 10 is an example of an information processing apparatus that transmits a request to the server 30.

The client apparatus 10 is, for example, a smartphone, a tablet terminal, or a personal computer.

The server 30 is an example of an information processing apparatus that provides the client apparatus 10 with a response corresponding to the request transmitted from the client apparatus 10.

The server 30 is, for example, a web server.

The log device 50 retrieves at least one of information (hereinafter referred to as "environment information") on the environment where the user stays, information (hereinafter referred to as "action information") on the user's action, and information (hereinafter referred to as "mental and physical information") on the user's mind-body).

The log device 50 is, for example, a wearable device that is wearable for the user.

The log device 50 is connected to the client apparatus 10 by wire or wireless.

The prediction information providing server 70 is an example of an information processing apparatus that provides prediction information indicating future prediction.

For example, the prediction information providing server 70 provides the following information:
  environment prediction information indicating prediction of future environment (for example, weather forecast);
  behavior prediction information indicating prediction (for example, schedule) of future user's action; and
  prediction of future user mind-body (for example, prediction of sexual cycle)

(1-1) Configuration of Client Apparatus the Configuration of the Client Apparatus 10 Will be Described with Reference to FIG. 1.

As shown in FIG. 1, the client apparatus 10 includes a memory 11, a processor 12, an input/output interface 13, a communication interface 14, and a GPS module 15.

The memory 11 is configured to store a program and data.

The memory 11 is, for example, a combination of a ROM (read only memory), a RAM (random access memory), and a storage (for example, a flash memory or a hard disk).

The program includes, for example, the following programs:
  OS (Operating System) program; and
  application (for example, web browser) program that executes information processing.

Data includes, for example, the following data:
  database referenced in information processing;
  data generated by executing information processing (that is, execution result of information processing)

The processor 12 is configured to activate a program stored in the memory 11 to realize the function of the client apparatus 10.

The processor 12 is an example of a computer.

The input/output interface 13 is configured to receive a user instruction from an input apparatus connected to the client apparatus 10, retrieve information from the log device 50, and output information to an output apparatus connected to the client apparatus 10.

The input device is, for example, a keyboard, a pointing device, a touch panel, or a combination thereof.

The output device is, for example, a display.

The communication interface 14 is configured to control communication between the client apparatus 10 and the server 30.

The GPS module 15 is configured to retrieve position information of the client apparatus 10 by communicating with a GPS (Global Positioning System) satellite.

(1-2) Configuration of Server

The configuration of the server 30 will be described with reference to FIG. 1.

As shown in FIG. 1, the server 30 includes a memory 31, a processor 32, and a communication interface 34.

The memory 31 is configured to store a program and data.

The memory 31 is, for example, a combination of ROM, RAM, and storage (for example, flash memory or hard disk).

The program includes the following program, for example:
  OS program; and
  application program for executing information processing.

The data includes, for example, the following data:
  database referred to in information processing; and
  execution result of information processing The processor 32 is configured to realize the function of the server 30 by activating a program stored in the memory 31.

The processor 32 is an example of a computer.

The input/output interface 33 is configured to receive a user instruction from an input apparatus connected to the server 30 and to output information to an output apparatus connected to the server 30.

The input device is, for example, a keyboard, a pointing device, a touch panel, or a combination thereof.

The output device is, for example, a display.

The communication interface 34 is configured to control communication between the server 30 and the client apparatus 10.

(1-3) Application

The application of the present embodiment will be described.

Figure 2:
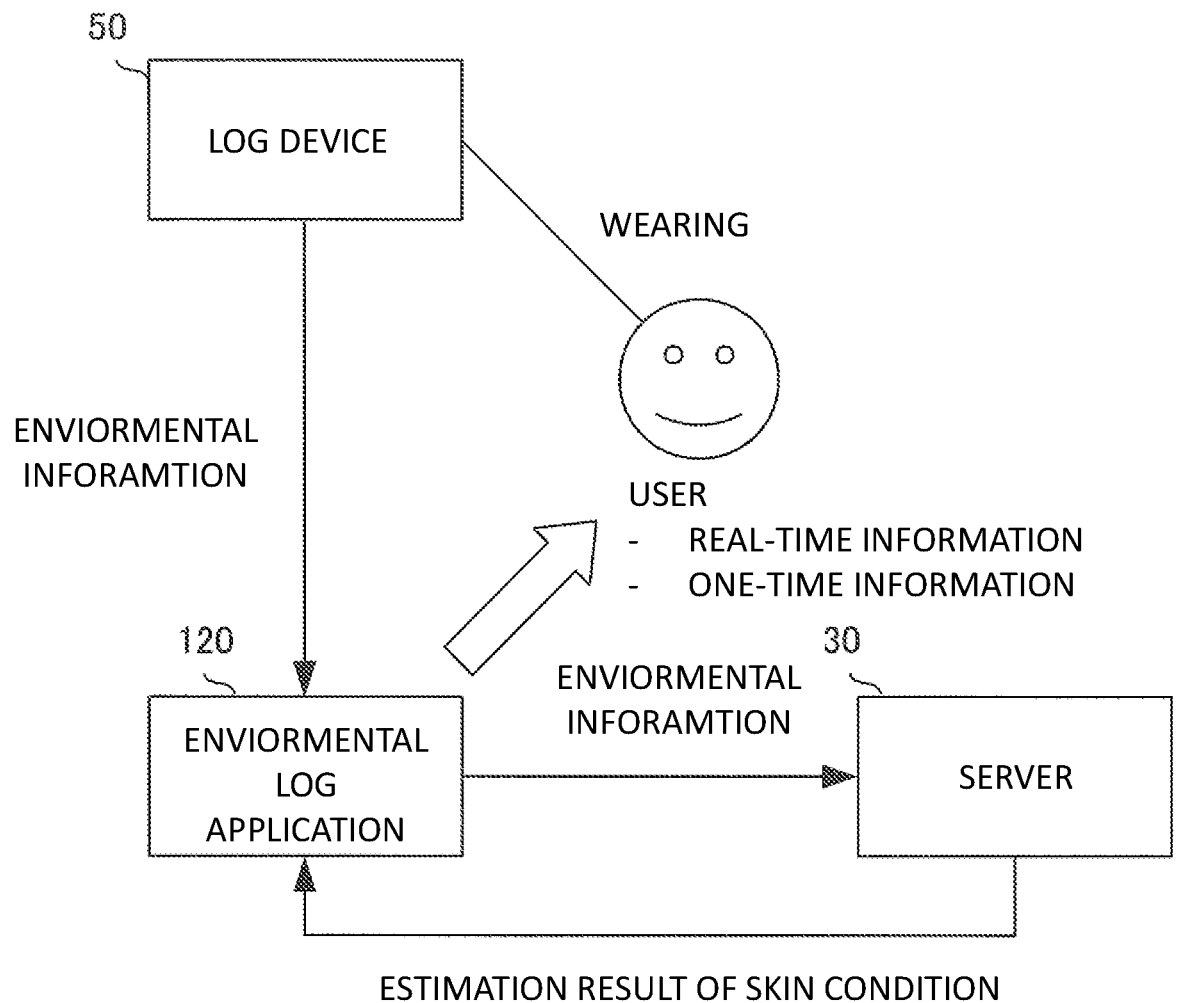
FIG. 2 is an explanatory diagram of an application according to the present embodiment.

FIG. 2 is an explanatory diagram of an application of the present embodiment.

The processor 12 (FIG. 1) executes the environment log application 120 (FIG. 2).

The environment log application 120 has the following functions:
  a function of retrieving environmental information from the log device 50;
  a function of transmitting environmental information to the server 30;
  a function of receiving skin condition estimation result based on information (hereinafter referred to as "environment log information") indicating the history of environmental information; and
  a function of presenting two types of information (real-time information (an example of first information) and one-time information (an example of second information)) based on the skin condition estimation result to the user.

(2) Database

The database of the present embodiment will be described.

The following database is stored in the memory 31.

(2-1) User Information Database

The user information database of the present embodiment will be described.

FIG. 3 is a diagram illustrating a data structure of the user information database according to the present embodiment.

The user information database shown in FIG. 3 stores information (hereinafter referred to as "user information") on users.

The user information database includes a "user ID" field, a "user name" field, a "user attribute" field, and an "estimation formula" field.

Each field is associated with each other.

The "user ID" field stores a user ID for identifying the user.

The "user name" field stores information (for example, text) indicating the user name.

The "user attribute" field stores information (hereinafter referred to as "user attribute information") related to user attributes.

The user attribute information is information arbitrarily determined by the user.

The "user attribute" field includes a "gender" field and an "age" field.

The "gender" field stores information indicating the gender of the user.

The "age" field stores information indicating the age of the user.

The "estimation formula" field stores an estimation formula (formula 1) for estimating the user's skin condition.

The estimation formula includes a coefficient for each factor that affects the user's skin.

$$f = a \times T + b \times M + c \times UV \qquad \text{(Equation 1)}$$

"f" is a score (hereinafter referred to as "skin score") indicating the estimation result of skin condition.
"a" is a temperature coefficient
"T" is temperature
"b" is humidity coefficient
"M" is humidity
"c" is UV exposure coefficient
"UV" is UV exposure amount An estimation formula is prepared for each index (hereinafter referred to as "skin index") of the user's skin condition.

That is, the coefficient included in the estimation formula is different for each skin index.

The skin index is, for example, at least one of the following:
stratum corneum moisture;
skin texture;
skin color;
dry skin;
skin smoothness;
transparent skin;
skin whitening;
rough skin;
skin inflammation; and
skin wrinkles.

(2-2) Environmental Log Information Database

The environmental log information database of the present embodiment will be described.

FIG. 4 is a diagram illustrating a data structure of the environment log information database according to the present embodiment.

The environment log information database shown in FIG. 4 stores environment log information.

The environment log information is information retrieved from the log device 50.

The environmental log information database includes an "environment log ID" field, a "date and time" field, an "UV exposure" field, a "temp" field, and a "hum" field.

Each field is associated with each other.

The environment log information database is associated with the user ID.

The "environment log ID" field stores an environment log ID for identifying environment information constituting the environment log information.

The "date and time" field stores information indicating the date and time when the environment information is retrieved.

The "UV exposure" field stores information indicating the amount of ultraviolet rays exposed to the user (hereinafter referred to as "UV exposure").

The "temp" field stores information indicating the temperature of the environment where the user stays.

The "hum" field stores information indicating the humidity of the environment where the user stays.

(2-3) Action Log Information Database

The action log information database of the present embodiment will be described.

FIG. 5 is a diagram illustrating a data structure of the action log information database according to the present embodiment.

The action log information database shown in FIG. 5 stores information indicating the history of action information (hereinafter referred to as "action log information").

The action log information is information retrieved from the log device 50, information determined according to a user instruction (for example, a user's answer to a questionnaire or a user's voluntary input), or a combination thereof.

The action log information database includes an "action log ID" field, a "date and time" field, an "action" field, a "start time" field, an "end time" field, a "calorie change" field, and a "position information" field.

Each field is associated with each other.

The action log information database is associated with the user ID.

In the "behavior log ID" field stores an action log ID for identifying the action information constituting the action log information.

The "date and time" field stores information indicating the date and time when the action information is retrieved.

The "action" field stores information on the user's action.

The user's action includes at least one of the following:
meal (for example, the content of meal);
exercise (for example, the kind of exercise);
sleep (for example, the number of wakeups during sleep): and
care action (for example, information on whether or not morning washing has been performed, on whether or not skin care has been performed, on the kind of the care, and on the product used for the care).

The "start time" field stores information indicating the start time of the action.

The "end time" field stores information indicating the end time of the action.

The "calorie change" field stores information indicating the calorie intake or the calorie consumption corresponding to the action.

The "position" field stores position information retrieved by the GPS module 15.

(2-4) Mind-Body Log Information Database

The mind-body log information database of the present embodiment will be described.

FIG. 6 is a diagram showing a data structure of the mind-body log information database according to the present embodiment.

The mind-body log information database shown in FIG. 6 stores information on the history of the user's mind-body information (hereinafter referred to as "mind-body log information").

The mind-body log information depends on information retrieved from the log device 50, a user instruction (for example, a user's answer to a questionnaire), or a combination thereof.

The mind-body log information database includes a "mind-body log ID" field, a "date and time" field, a "pulse" field, a "sexual cycle" field, and a "stress" field.

Each field is associated with each other.

The mind-body log information database is associated with the user ID.

The "mind-body log ID" field stores a mind-body log ID for identifying mind-body information constituting the mind-body log information.

The "date and time" field stores information indicating the date and time when the mind-body information is retrieved.

The "pulse" field stores the pulse value of the user.

The pulse value is information retrieved from the log device 50, for example.

The "sexual cycle" field stores information indicating an sexual cycle (an example of hormone balance information).

The "stress" field stores stress information indicating an index of stress. The stress information indicates, for example, the intensity of stress, the factor of stress, the type of stress, or a combination thereof.

The stress information depends on the pulse value, the sexual cycle, or a combination thereof (2-5) Skin Evaluation Log Information Database The skin evaluation log information database of the present embodiment will be described.

FIG. 7 is a diagram illustrating a data structure of the skin evaluation log information database according to the present embodiment.

The skin evaluation log information database in FIG. 7 stores information (hereinafter referred to as "skin evaluation log information") indicating a history of qualitative evaluation (hereinafter referred to as "skin evaluation") regarding the skin condition.

The skin evaluation log information database includes a "skin evaluation log ID" field, a "date and time" field, and a "skin score" field.

Each field is associated with each other.

The skin evaluation log information database is associated with the user ID.

The "skin evaluation log ID" field stores a skin evaluation log ID for identifying the skin evaluation constituting the skin evaluation log information.

The "date and time" field stores information indicating the date and time when the skin evaluation is generated.

The "skin score" field stores the skin score obtained from the environment information and the estimation formula.

The "skin score" field includes a "first skin score" field and a "second skin score" field.

The "first skin score" field stores a first skin score (an example of a first skin index).

The first skin score indicates the current skin condition estimated from the environment log information (for example, when environment information is retrieved).

The "second skin score" field stores a second skin score (an example of a second skin index).

A second skin score shows the skin condition of the future estimated from environmental log information and environmental prediction information (for example, one week after the day when environmental information is retrieved).

(2-6) Content Matching Table

The content matching table of the present embodiment will be described.

FIG. 8 is a diagram showing the data structure of the content matching table of the present embodiment.

The content matching table in FIG. 8 has a data structure indicating the relationship between the skin evaluation and the content of two types of information (real-time information and one-time information) to be presented to the user.

The content matching table includes a "reference score" field, a "real-time content" field, and a "one-time content" field.

The "reference score" field stores a reference score for specifying real-time content or one-time content.

The "real-time content" field stores a content ID for identifying real-time content constituting real-time information.

The real-time content is, for example, text, image, sound, URL (Uniform Resource Locator), or a combination thereof.

Real-time content includes the following examples:
  message prompting to take care immediately;
  advice on an immediate care method;
  advice on products suitable for care (for example, URL of website for purchasing the product); and
  first skin score showing past skin condition.

The "one-time content" field stores a content ID for identifying one-time content constituting the one-time information.

One-time content is, for example, text, images, sounds, URL, or combinations thereof.

The one-time content includes, for example, the following:
  messages prompting one to take care before going to bed
  advice on a method to take care before going to bed;
  advice (for example, the URL of the website for purchasing the product) on products suitable for care; and
  skin score indicating skin condition of future skin.

(2-7) Task Information Database

The task information database of the present embodiment will be described.

FIG. 9 is a diagram showing the data structure of the task information database of the present embodiment.

The task information database shown in FIG. 9 stores information (hereinafter referred to as "task information") related to care actions to be performed by the user.

The task information database includes a "task ID" field, a "reference content" field, a "registration date and time" field, and an "end date and time" field.

Each field is associated with each other.

The task information database is associated with the user ID.

The "task ID" field stores a task ID for identifying task information.

The "reference content" field stores a content ID for identifying reference content (real-time content or one-time content) to be referred as a reference for care action.

The "registration date and time" field stores information indicating the date and time when the task information is registered in the task information database.

The "end date and time" field stores information indicating the date and time when the care action corresponding to the task information is ended.

The code "NOT" means that the care action has not ended.

(3) Information Processing

The information processing of the present embodiment will be described.

(3-1) Content Presentation Processing

Content presentation processing according to the present embodiment will be described.

Figure 10:
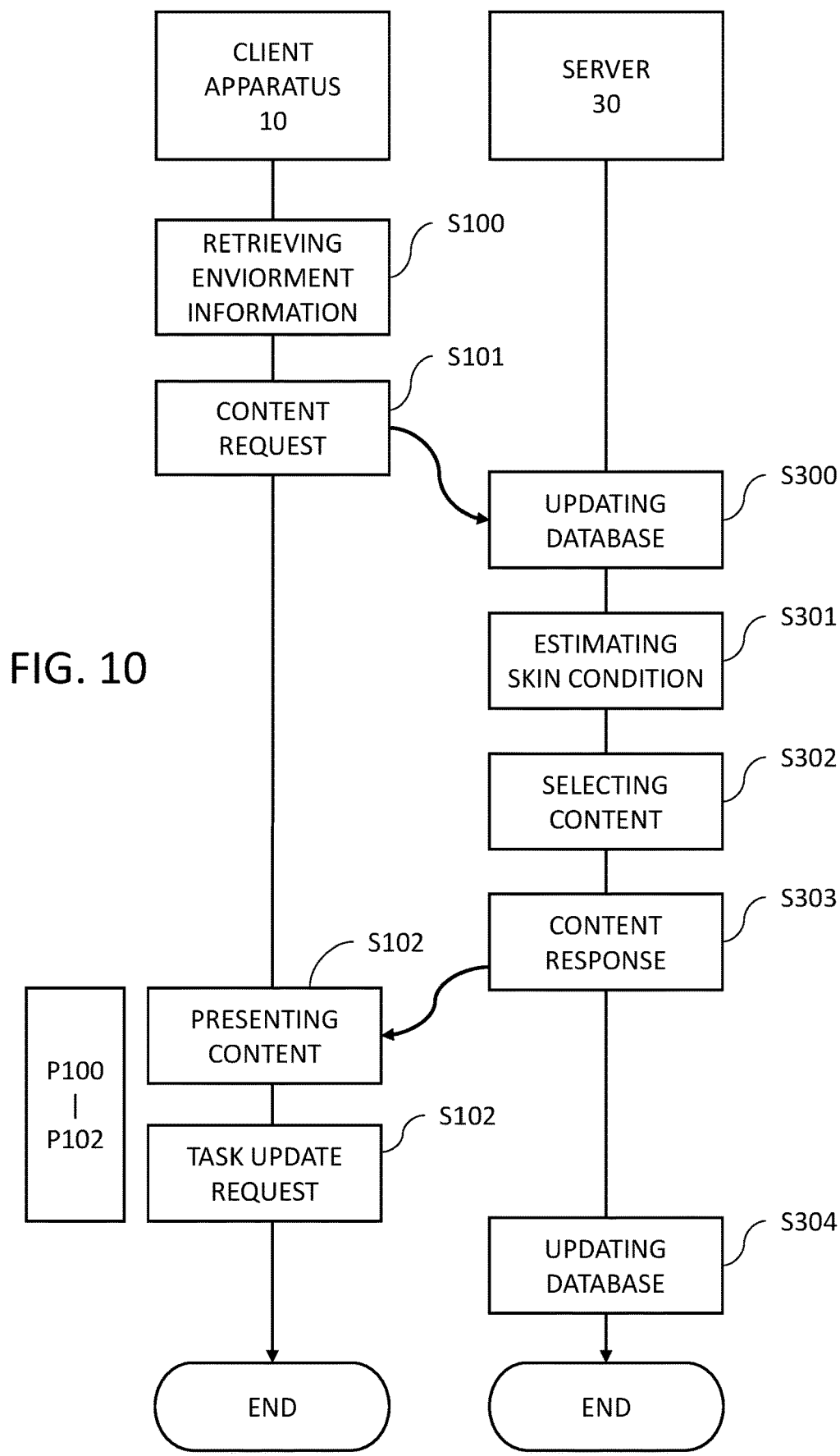
FIG. 10 is a sequence diagram of content presentation processing according to the embodiment.

FIG. 10 is a sequence diagram of content presentation processing according to the present embodiment.

Figure 11:
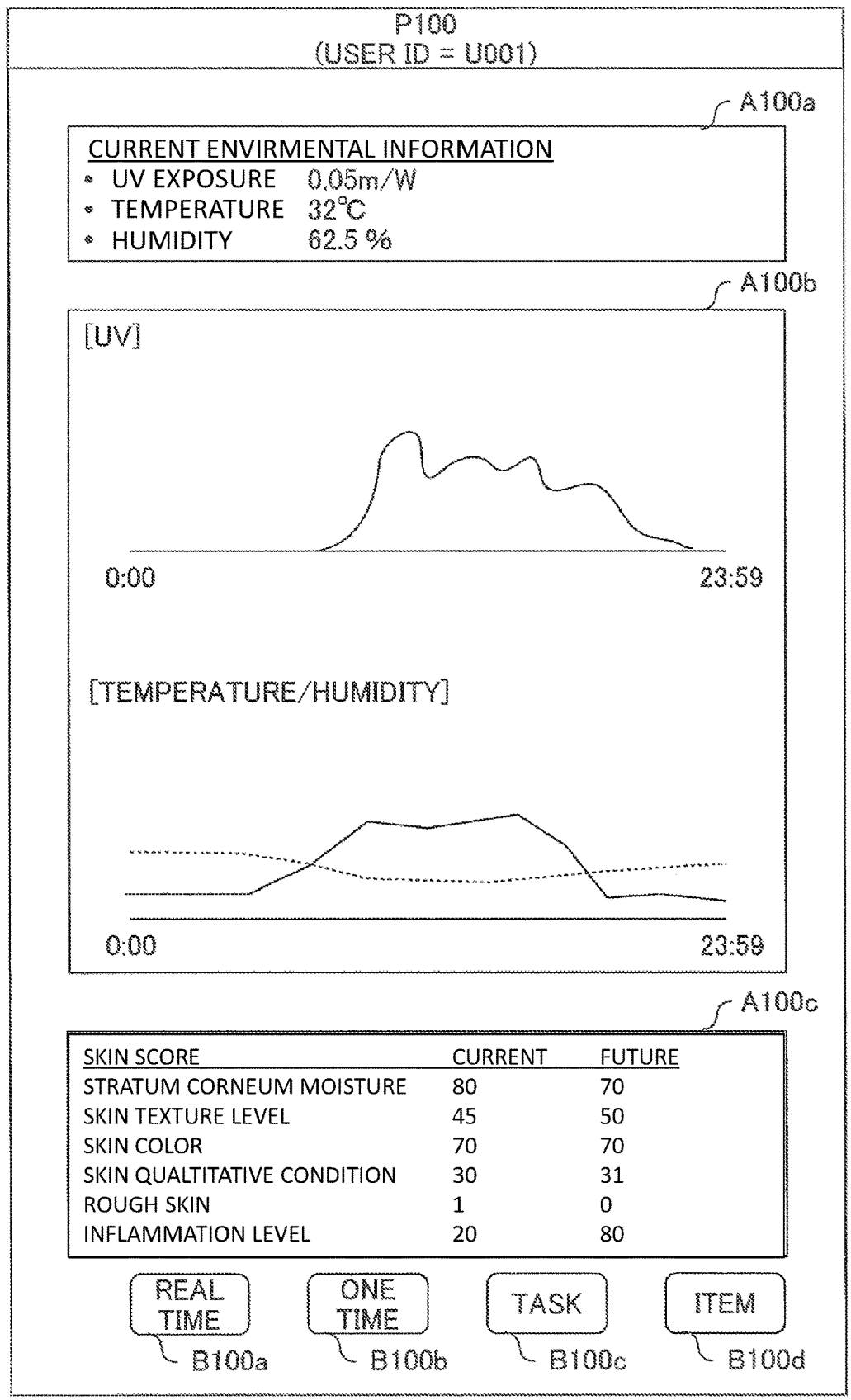
FIG. 11 is a diagram showing an example of a screen displayed in the information processing of FIG. 10.

FIGS. 11 and 12 are diagrams illustrating examples of screens displayed in the information processing of FIG. 10.

As shown in FIG. 10, the client apparatus 10 executes retrieving environment information (S100).

Specifically, the processor 12 retrieves environmental information (for example, information indicating the UV exposure amount, temperature, and humidity) from the log device 50 at every constant time.

The processor 12 stores the environment information in association with the information indicating the execution date and time of step S100 (that is, the date and time when the environment information is retrieved) in the memory 11.

After step S100, the client apparatus 10 executes a content request (S101).

Specifically, the processor 12 transmits content request data to the server 30.

The content request data includes the following information:
- user ID;
- environment information; and
- information indicating the execution date and time of step S100.

After step S101, the server 30 executes updating database (S300) based on the content request data.

Specifically, the processor 32 adds a new record to the environment log information database (FIG. 4) associated with the user ID included in the content request data.

The following information is stored in each field of the new record.
- "environment log ID" field stores one environment log ID.
- "date and time" field stores information indicating the execution date and time of step S100 included in the content request data.
- "UV exposure" field stores the information indicating UV exposure amount included in the content request data.
- "temp" field stores the information indicating temperature included in the content request data.
- "hum" field stores the information indicating humidity included in the content request data.

Thereby, the environment information retrieved in step S100 is stored in the server 30.

After step S300, the server 30 executes estimating skin condition (S301).

Specifically, the processor 32 refers to the user information database (FIG. 3) and identifies an estimation formula associated with the user ID included in the content request data.

The processor 32 specifies a record (Hereinafter referred to as "environment reference record") among the records of the environment log information database updated in step S300. The environment reference record includes the value of "date and time" field back to the execution date of step S100 for a certain period (for example, one week).

The processor 32 calculates the average value of the "UV exposure" field, the "temp" field, and the "hum" field in the environment reference record.

The processor 32 calculates the first skin score by applying the calculated average value to the specified estimation formula.

The first skin score is calculated for each of the following indexes:
- skin score related to stratum corneum moisture;
- skin score related to texture;
- skin score related to skin color;
- skin score related to qualitative skin condition;
- skin score related to rough skin;
- skin score related to inflammation level; and
- skin score related to the level of fine lines.

The processor 32 retrieves environment prediction information from the prediction information providing server 70.

The processor 32 calculates the second skin score by applying the average value of the values of the "UV exposure" field, the "temp" field, and the "hum" field of the environment reference record, and the environment prediction information to the specified estimation formula.

The second skin score is calculated for each index at the same as the first skin score.

The processor 32 adds a new record to the skin evaluation log information database (FIG. 7) associated with the user ID included in the content request data.

The following information is stored in each field of the new record.
- "skin evaluation log ID" field stores new skin evaluation log ID.
- "date and time" field stores information indicating the execution date and time of step S100.
- "first skin score" field stores the first skin score.
- "second skin score" field stores the second skin score.

After step S301, the server 30 executes selecting content (S302).

Specifically, the processor 32 refers to the "reference score" field of the content matching table (FIG. 8) and specifies the content ID corresponding to the first skin score calculated in step S301.

For example, in the case of the first skin score "30", the content ID "REAL001" associated with the reference score "20 to 39" is specified.

The processor 32 refers to the "reference score" field and specifies the content ID corresponding to the second skin score calculated in step S301.

For example, in the case of the second skin score "60", the content ID "ONE003" associated with the reference score "60 to 89" is specified.

After step S302, the server 30 executes a content response (S303).

Specifically, the processor 32 transmits content response data to the client apparatus 10.

The content response data includes the following information:
- first skin score and second skin score calculated in step S301;
- environmental information referred to in calculating the first skin score in step S301;
- environment log information referred to in calculating the second skin score in step S302; and
- content ID specified in step S302 and content (real-time content or one-time content) identified by the content ID.

After step S303, the client apparatus 10 executes presenting content (S102) based on the content response data.

Specifically, the processor 12 displays the screen P100 (FIG. 12) on the display.

Screen P100 includes display objects A100a to A100d and button objects B100a to B100d.

The display object A100d displays the environmental information (UV exposure amount, temperature, and humidity) stored in the memory 11 in step S100.

The display object A100b displays a graph (for example, a graph showing temporal changes in the UV exposure amount, temperature, and humidity) corresponding to the environment log information included in the content response data.

The display object A100c displays a first skin score and a second skin score included in the content response data.

Figure 12A:
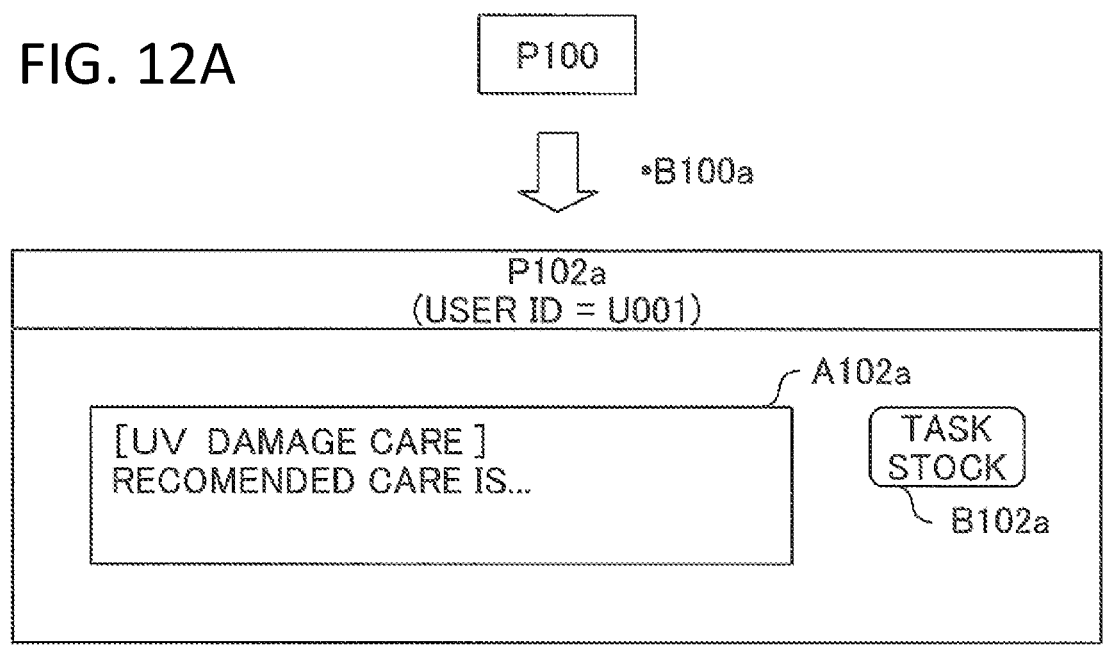
FIG. 12 is a diagram showing an example of a screen displayed in the information processing of FIG. 10.

The button object B100a is an object that receives a user instruction for displaying the real-time content screen P102a (FIG. 12A).

Figure 12B:
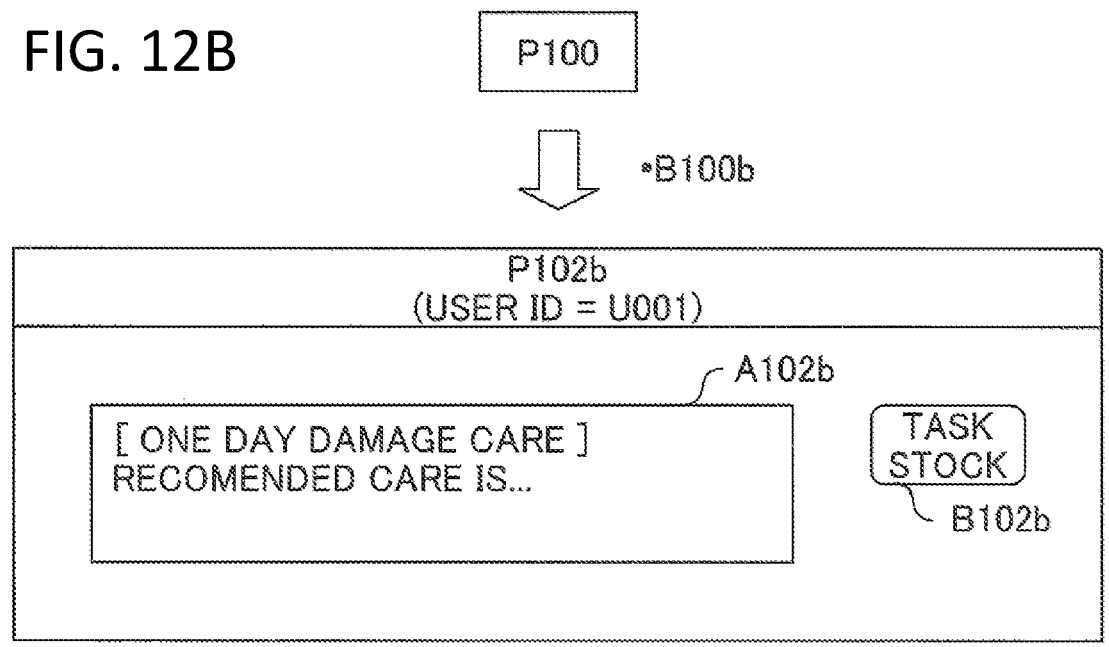

The button object B100b is an object that receives a user instruction for displaying the one-time content screen P102b (FIG. 12B).

Figure 13:
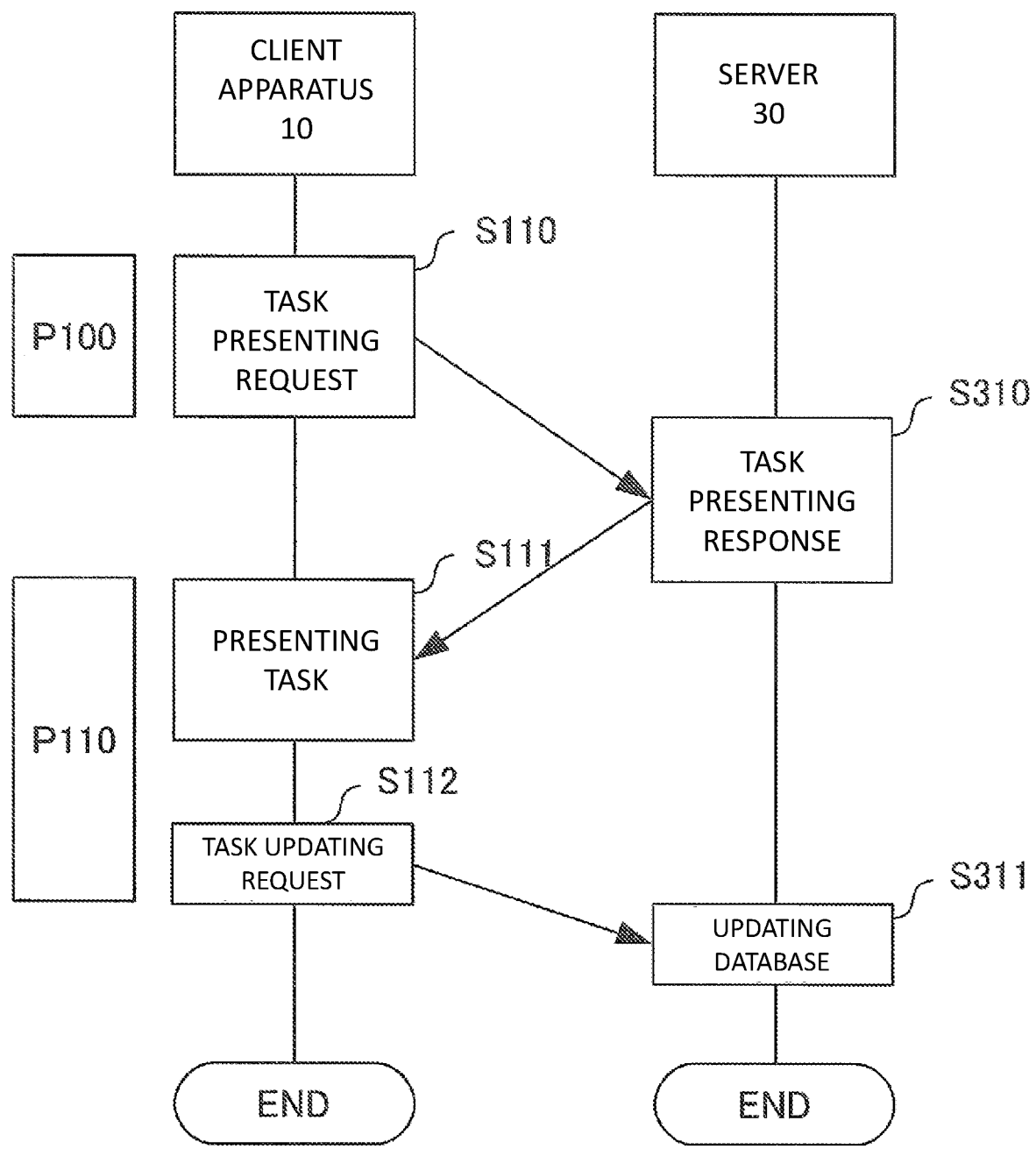
FIG. 13 is a sequence diagram of task update processing according to the present embodiment.

The button object B100c is an object that receives a user instruction for presenting a task (S111 in FIG. 13).

The button object B100d is an object that receives a user instruction for accessing a shopping site for purchasing a care item useful for care according to real-time content or one-time content.

When the user designates the button object B100a, the processor 12 displays the screen P102a (FIG. 12A) on the display.

The screen P102a includes a display object A102a and a button object B102a.

The display object A102a displays real-time content identified by the content ID included in the content response data.

The button object B102a is an object that receives a user instruction for notifying the server 30 that the care indicated by the real-time content displayed on the display object A102a is finished.

When the user designates the button object B100b, the processor 12 displays the screen P102b (FIG. 12B) on the display.

The screen P102b includes a display object A102b and a button object B102b.

The display object A102b displays one-time content identified by the content ID included in the content response data.

The button object B102b is an object that receives a user instruction for notifying the server 30 that the care indicated by the one-time content displayed on the display object A102b is finished.

After step S102, the client apparatus 10 executes a task update request (S103).

As a first example, when the user designates the button object B102a (FIG. 12A), the processor 12 transmits task update request data to the server 30.

The task update request data includes the following information:
user ID;
content ID of the real-time content displayed on the display object A102a; and
information indicating the execution date and time of step S103.

As a second example, when the user designates the button object B102b (FIG. 12B), the processor 12 transmits the task update request data to the server 30. The task update request data includes the following information:
user ID;
content ID of the one-time content displayed on the display object A102b;
information indicating the execution date and time of step S103

After step S103, the server 30 executes database update (S304).

Specifically, the processor 32 adds a new record to the task information database (FIG. 9) associated with the user ID included in the task update request data.

The following information is stored in each field of the new record:
"task ID" field: new task ID;
"content ID" field: content ID included in task update request data
"registration date and time" field: information indicating the execution date and time of step S103 included in task update request; and
"end date and time" field: code "NOT".

Thereby, the task specified by the user on the screen P102a or P102b (FIG. 12) is recorded in the server 30.

(3-2) Task Update Processing

The task update processing of the present embodiment will be described.

FIG. 13 is a sequence diagram of task update processing according to the present embodiment.

Figure 14:
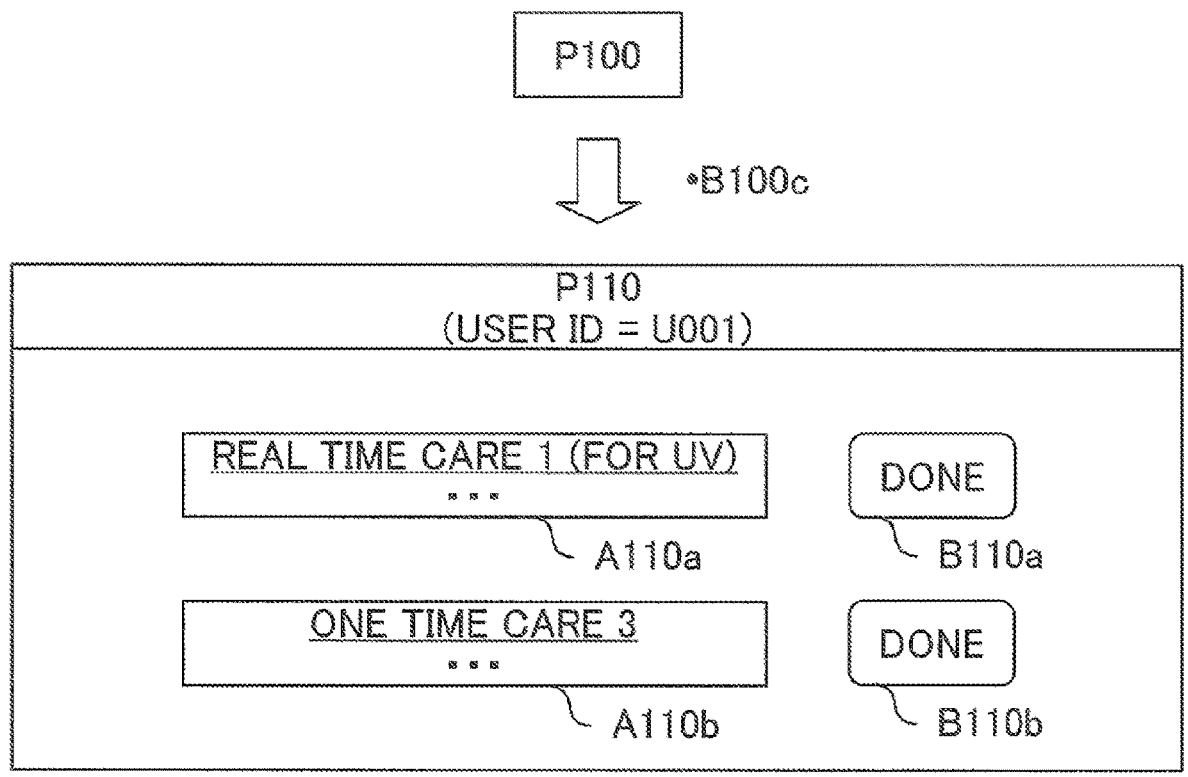
FIG. 14 is a diagram showing an example of a screen displayed in the information processing of FIG. 13.

FIG. 14 is a diagram illustrating an example of a screen displayed in the information processing of FIG.

As shown in FIG. 13, the client apparatus 10 executes a task presentation request (S110).

Specifically, when the user designates the button object B100c (FIG. 11), the processor 12 transmits task presentation request data to the server 30.

The task presentation request data includes a user ID.

After step S110, the server 30 executes a task presentation response (S310).

Specifically, the processor 32 refers to the task information database (FIG. 9) associated with the user ID included in the task presentation request data, and specifies the task ID and the content ID of the records (that is, the records storing the task information regarding the unfinished task) in which the code "NOT" is stored in the "end date and time" field.

The processor 32 transmits task presentation response data to the client apparatus 10.

The task presentation response data includes the following information:
task ID of unfinished task; and
content ID associated with task ID of unfinished task.

After step S310, the client apparatus 10 presents a task (S111).

Specifically, the processor 12 displays the screen P110 (FIG. 14) on the display based on the task presentation response data.

The screen P110 includes display objects A110a to A110b and button objects B110a to B110b.

The display objects A110a to A110b displays the content identified by the content ID included in the task presentation response data.

The button objects B110a to B110b are objects that receive user instructions for notifying the server 30 of the end of tasks corresponding to the content displayed on the display objects A110a to A110b, respectively.

The button objects B110a to B110b are assigned task IDs associated with content IDs for identifying the content displayed on the display objects A110a to A110b, respectively.

After step S111, the client apparatus 10 executes a task update request (S112).

Specifically, when the user designates the button object B110a (FIG. 14), the processor 12 transmits task update request data to the server 30.

The task update request data includes the following information:

user ID;
task ID assigned to the button object B110a designated by the user; and
information indicating the execution date and time of step S112.

After step S112, the server 30 executes update of the database (S311).

Specifically, the processor 32 specifies a task information database (FIG. 9) associated with the user ID included in the task update request data.

The processor 32 specifies a record including the task ID included in the task update request data in the specified task information database.

The processor 32 stores information indicating the execution date and time of step S112 included in the task update request data in the "end date and time" field of the specified record.

The processor 32 specifies the action log information database (FIG. 5) associated with the user ID included in the task update request data.

The processor 32 adds a new record to the identified action log information database.

The following information is stored in each field of the new record:

"action log ID" field: new action log ID;
"date and time" field: information indicating the execution date and time of step S112 included in the task update request data; and
"action" field: task ID included in the task update request data.

Thus, the end of the task designated by the user on the screen P110 (FIG. 14) and the care action to end the task are recorded in the server 30.

(3-3) Estimation Formula Correction Processing

The estimation formula correction processing of the present embodiment will be described.

Figure 15:
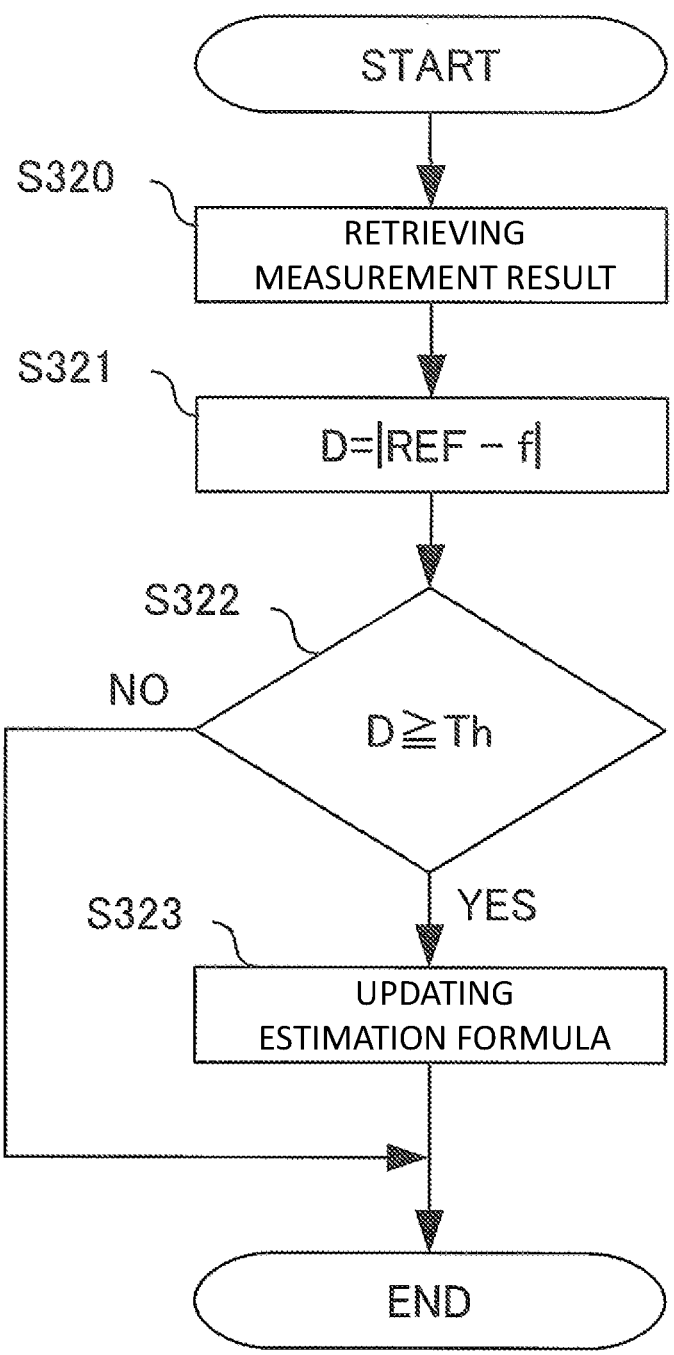
FIG. 15 is a flowchart of processing for correction of an estimation formula according to the present embodiment.

FIG. 15 is a flowchart of the process of correction module the estimation formula according to the present embodiment.

The processing of FIG. 15 is executed after the user ID of the user is registered in a dedicated measuring apparatus (for example, an apparatus disposed in a cosmetic store).

As shown in FIG. 15, the server 30 executes retrieving measurement result (S320).

Specifically, when the user measures the reference value REF regarding the skin condition using the dedicated measuring apparatus (for example, an apparatus disposed in a cosmetics store), the processor 32 retrieves the user ID, the reference value REF from the measuring apparatus.

After step S320, the server 30 calculates a difference value (hereinafter referred to as "deviation value") D between the reference value REF and the skin score of using Expression 2 (S321).

$$D=|REF-f|$$ (Expression 2)

When the deviation value D calculated in step S321 is less than the predetermined threshold Th (S322—NO), the process in FIG. 15 ends.

When the deviation value D calculated in step S321 is equal to or greater than the predetermined threshold Th (S322—YES), the server 30 executes the update of the estimation formula (S323).

Specifically, the processor 32 changes the coefficient of the estimation formula (FIG. 3) associated with the user ID retrieved in step S320 so that the deviation value D is less than the predetermined threshold Th.

Thereby, the estimation formula is adjusted for each user.

The process of FIG. 15 is executed for each skin index.

(4) Variations

Variations of the present embodiment will be described.

(4-1) Variation 1 Variation 1 Will be Described.

Variation 1 is an example in which a content presentation process (FIG. 10) is executed using a combination of environment log information (FIG. 4) and action log information (FIG. 5).

Specifically, the estimation formula of variation 1 includes a coefficient of user's action and a parameter determined according to action information.

In step S301 (FIG. 10), the processor 32 specifies an action reference record of the action log information database (FIG. 5) associated with the user ID included in the content request data in step S100. The "date and time" field of the specified action reference record has a value included in a certain period (for example, one week) retroactively from the execution date.

The processor 32 calculates first skin score by applying an average value calculated from the environment reference record and at least one of the "action" field, the "start time" field, the "end time" field, the "calorie change" field, and the "position" field of the action reference record to the estimation formula.

A first skin score shows the present skin condition estimated from environmental log information and action log information.

The processor 32 retrieves action prediction information from the prediction information providing server 70.

The processor 32 calculates the second skin score by applying at least one information of the "action" field, "start time" field, "end time" field, "calorie change" field, and "position" field of the action reference record, an average value of the environment reference record, and the action prediction information to the estimation formula.

A second skin score shows the future skin condition estimated from environmental log information, action log information, and action prediction information.

The real-time content and the one-time content further include advice on the user's action.

According to the first variation, the skin condition may be estimated in consideration of both the environment where the user stays and the user's action.

Thereby, the content according to the combination of environmental log information and action log information may be provided.

(4-2) Variation 2 Modification 2 Will be Described.

Variation 2 is an example in which the content presentation process (FIG. 10) is executed using a combination of environment log information (FIG. 4) and mind-body log information (FIG. 6).

Specifically, the estimation formula of Variation 2 includes a user's mind-body coefficient and a parameter depending on mind-body log information.

In step S301 (FIG. 10), the processor 32 specifies a mental and physical reference record of the mind-body log information database (FIG. 6) associated with the user ID included in the content request data in step S100. The "date and time" field of the mental and physical reference record has a value included in a certain period (for example, one week) retroactively from the execution date.

The processor 32 calculates the first skin score by applying at least one of the "pulse" field, the "sexual cycle" field, and the "stress" field of the mind-body reference record and the average value calculated from the environment reference record to the estimation formula.

The first skin score indicates the current skin condition estimated from the environment log information and the mind-body log information.

The processor 32 retrieves mind-body prediction information from the prediction information providing server 70.

The processor 32 calculates the second skin score by applying at least one information of the "pulse" field, the "sexual cycle" field, and the "stress" field of the mind-body reference record, the average value calculated from the environment reference record, and the mind-body prediction information to the estimation formula.

A second skin score shows the future skin condition estimated from environmental log information, mind-body log information, and mind-body prediction information.

The real-time content and the one-time content further include the following information:

advice on user's hormone balance; and advice on user's stress.

According to the second variation, the skin condition may be estimated in consideration of both the environment where the user stays and the mind-body of the user.

Thereby, the content according to the combination of environmental log information and mind-body log information may be provided.

(4-3) Variation 3

Variation 3 will be described.

Variation 3 is an example in which the future skin condition is estimated in consideration of the user's care action.

Specifically, the estimation formula of variation 3 includes a coefficient of the user's care action and a parameter depending on the task information.

In step S301 (FIG. 10), after calculating the average value, the processor 32 refers to the task information database (FIG. 9) associated with the user ID included in the content request data to specify a record (hereinafter referred to as "reference record") within a certain period (for example, within one week retroactively from the execution date of step S301).

The processor 32 calculates the second skin score by applying the information of the identified reference record (that is, information regarding the care action within a certain period) and the calculated average value to the estimation formula.

According to the variation 3, the future skin condition is estimated in consideration of the history of the user's care action.

Thereby, the future skin condition suitable for each user may be presented.

(4-4) Variation 4 Variation 4 Will be Described.

Variation 4 is an example in which the skin score is output to an external apparatus other than the client apparatus 10.

Specifically, the server 30 is connected to a cosmetic generation apparatus that generates cosmetics based on the skin score.

A plurality of cartridges is arranged in the cosmetic generation apparatus.

Each cartridge contains a raw material as a cosmetic ingredient or a mixture of the raw materials (hereinafter referred to as "cosmetics").

The raw material is, for example, a liquid, a powder, a solid, or a combination thereof.

In step S301 (FIG. 10), the processor 32 transmits the first skin score and the second skin score to the cosmetic generation apparatus.

The cosmetic generation apparatus determines the usage amount of the raw material or the cosmetic contained in each cartridge based on at least one of the first skin score and the second skin score transmitted from the server 30.

The cosmetic generation apparatus disposes the determined usage amount of raw material or cosmetic from each cartridge to provide it to the user.

According to the variation 4, the user may be provided with cosmetics generated using raw materials or cosmetics according to the environmental information.

(4-5) Variation 5

Variation 5 will be described.

Variation 5 is an example in which a notification message is presented to the user when the environmental information satisfies a predetermined condition.

Specifically, the processing of FIG. 10 is executed while the environment log application 120 is operating in the background.

When the environment information retrieved in step S100 satisfies the predetermined condition, the processor 12 displays a screen including a notification message on the display.

The predetermined condition is at least one of the following.

UV exposure amount is a predetermined value or more.

Temperature is a predetermined value or more.

Humidity is a predetermined value or less.

The user may immediately know that the user stays in an environment that adversely affects the skin.

(5) Summary of the Present Embodiment

This embodiment will be summarized as below.

The information processing apparatus (for example, the server 30) according to the first aspect of the present embodiment includes:

a retrieve module (for example, the processor 32 executing step S300) configured to retrieve environmental information indicating an ultraviolet ray exposure amount indicating an amount of ultraviolet rays exposed to a user, a temperature of an environment where the user stays, and a humidity of the environment where the user stays;

a present module (for example, the processor 32 executing step S303) configured to present first information (for example, real-time content) relating to the skin condition of the user based on the environmental information; and a present module (for example, the processor 32 executing step S303) configured to present second information (for example, one-time content) relating to the skin condition of the user based on environmental log information including a plurality of environmental information.

According to the first aspect, the user may receive real-time content based on current environment information and one-time content based on environment log information.

That is, the user may get optimal information in consideration of time-series environmental factors.

In the second aspect of the present embodiment, the first information and the second information comprise at least one of advice on the user's skin care method, advice on a product suitable for the user's skin care, advice on the user's hormone balance, and advice on the user's stress.

The information processing apparatus according to the third aspect of the present embodiment further includes:

an estimation module (for example, the processor 32 executing step S301) configured to estimate a skin index (for example, the first skin score and the second skin score) of the skin condition of the user based on the environment log information; and a present module (for example, the processor 32 executing step S303) configured to present the estimated skin index.

According to the third aspect, the user may know the skin condition based on the environmental information.

The information processing apparatus according to the fourth aspect of the present embodiment includes:

a retrieve module (for example, the processor 32 executing step S300) configured to retrieve environmental information indicating an ultraviolet ray exposure amount indicating an amount of ultraviolet rays exposed to a user, a temperature of an environment where the user stays, and a humidity of the environment where the user stays;

an estimation module (for example, the processor 32 executing step S301) configured to estimate a skin index of the skin condition of the user based on the environment log information comprising a plurality of the environmental information; and a present module (for example, the processor 32 executing step S303) configured to present the estimated skin index.

According to the fourth aspect, the user may know the first skin score based on the current environment information and the second skin score based on the environment log information.

That is, the user may get optimal information in consideration of time-series environmental factors.

The information processing apparatus according to the fifth aspect of the present embodiment includes a retrieve module (for example, the processor 32 executing step S300) configured to retrieve action log information indicating a history of action information relating to the user's action, wherein the estimation module estimates the skin index based on the environment log information and the action log information.

According to the fifth aspect, the user may know the skin condition based on both the environment where the user stays and the user's action.

The information processing apparatus according to the sixth aspect of the present embodiment includes a retrieve module (for example, the processor 32 executing step S300) configured to retrieve psychosomatic log information related to the user's mind-body, wherein the estimation module estimates the skin index based on the environment log information and the psychosomatic log information.

According to the sixth aspect, the user may know the skin condition based on both the environment where the user stays and the user's mind-body.

In the seventh aspect, it is provided with the information processing apparatus including comprising a retrieve module (for example, the processor 32 executing step S300) configured to retrieve psychosomatic log information related to the user's mind-body, wherein the estimation module estimates the skin index based on the environment log information and the psychosomatic log information.

According to the seventh aspect, the user can know the skin condition based on both the environment where the user stays and the environment where the user plans to stay.

In the information processing apparatus of the eighth aspect of the present embodiment, the retrieve module retrieves the environmental information from a measuring apparatus (for example the log device 50) configured to measure the environmental information.

The information processing apparatus according to the ninth aspect of the present embodiment further includes a present module configured to present a notification message when the amount of ultraviolet rays exposed to the user is equal to or greater than a predetermined value.

According to the ninth aspect, even if the user does not utilization the environment log application 120, the user may immediately know that the user is in an environment that adversely affects the skin.

The information processing apparatus (for example, the server 30) according to the tenth aspect of the present embodiment capable of communicate with the wearable device (for example, the log device 50) includes:

a retrieve module (for example, the processor 32 executing step S300) configured to retrieve information from the wearable device; and a present module (for example, the processor 32 executing step S302) configured to present advice on the skin care of the user wearing the wearable device and based on the information retrieved from the wearable device.

(6) Other Variations

Other modifications will be described.

The memory 11 may be connected to the client apparatus 10 via the network NW.

The memory 31 may be connected to the server 30 via the network NW.

Each step of the above information processing can be executed by either the client apparatus 10 or the server 30.

The environment log information and the action log information may be retrieved by a module built in the client apparatus 10.

The environment log information, the action log information, and the mind-body log information may be retrieved from an external server different from the server 30.

In step S301, estimation of one of the first skin score and the second skin score can be omitted.

Although the embodiments of the present invention have been described in detail above, the scope of the present invention is not limited to the above embodiments.

Further, various modifications and changes can be made to the above embodiments without departing from the spirit of the present invention.

In addition, the above embodiments and variations can be combined.

REFERENCE SIGNS LIST

1: Information processing system
10: Client device
11: Memory
12: Processor
13: Input/output interface
14: Communication interface
15: GPS module
30: Server
31: Memory
32: Processor
33: Input/output interface
34: Communication interface
50: Log device
70: Predictive information providing server 70
120: Environmental log application

The invention claimed is:

1. An information processing apparatus comprising:
a processor configured to:
retrieve environmental information indicating an ultraviolet ray exposure amount indicating an amount of ultraviolet rays exposed to a user, a temperature of an environment where the user stays, and a humidity of the environment where the user stays;

present first information relating to the skin condition of the user based on the environmental information;

present second information relating to the skin condition of the user based on environmental log information including a plurality of environmental information;

estimate a skin index of the skin condition of the user based on the environment log information;

present the estimated skin index; and retrieve environmental prediction information indicating a prediction of a future environment, wherein the processor estimates the skin index based on the environmental log information and the environmental prediction information.

2. The apparatus of claim 1, wherein the processor is further configured to:

retrieve action log information indicating a history of action information relating to the user's action, and estimate the skin index based on the environment log information and the action log information.

3. The apparatus of claim 2, wherein the user's action includes at least one of the user's having meal, the user's exercising, the user's sleeping, or the user's care action.

4. The apparatus of claim 1, wherein the processor is further configured to:

retrieve psychosomatic log information related to the user's at least one of the user's pulse, the user's sexual cycle, or the user's mind stress, and estimate the skin index based on the environment log information and the psychosomatic log information.

5. The apparatus of claim 1, wherein the processor is further configured to:

retrieve action prediction information indicating a prediction of a future user's action, and estimate the skin index based on the environmental log information, the environmental prediction information, and the action prediction information.

6. The apparatus of claim 1, wherein the processor is further configured to:

retrieve mind-body prediction information indicating a prediction of the user's mind-body, and estimate the skin index based on the environmental log information, the environmental prediction information, and the mind-body prediction information.

7. The apparatus of claim 6, wherein the mind-body prediction information indicates the user's at least one of the user's pulse prediction, the user's sexual cycle prediction, or the user's mind stress prediction.

8. The apparatus of claim 1, wherein the processor is further configured to present a notification message when the amount of ultraviolet rays exposed to the user is equal to or greater than a predetermined value.

9. A computer-implemented method comprising:

retrieving environmental information indicating an ultraviolet ray exposure amount indicating an amount of ultraviolet rays exposed to a user, a temperature of an environment where the user stays, and a humidity of the environment where the user stays;

presenting first information relating to the skin condition of the user based on the environmental information;

presenting second information relating to the skin condition of the user based on environmental log information including a plurality of environmental information;

estimating a skin index of the skin condition of the user based on the environment log information;

presenting the estimated skin index; and retrieving environmental prediction information indicating a prediction of a future environment, wherein the estimating estimates the skin index based on the environmental log information and the environmental prediction information.

10. The method of claim 9, wherein the first information and the second information comprise at least one of advice on the user's skin care method, advice on a product suitable for the user's skin care, advice on the user's hormone balance, or advice on the user's stress.

* * * * *